US007897931B2

(12) United States Patent
De Godzinsky

(10) Patent No.: US 7,897,931 B2
(45) Date of Patent: Mar. 1, 2011

(54) X-RAY IMAGING SENSOR AND X-RAY IMAGING METHOD

(75) Inventor: Christian De Godzinsky, Vantaa (FI)

(73) Assignee: Planmeca Oy, Helsinki (FI)

( * ) Notice: Subject to any disclaimer, the term of this patent is extended or adjusted under 35 U.S.C. 154(b) by 0 days.

(21) Appl. No.: 12/308,085

(22) PCT Filed: Jun. 5, 2007

(86) PCT No.: PCT/FI2007/050327

§ 371 (c)(1),
(2), (4) Date: Dec. 5, 2008

(87) PCT Pub. No.: WO2007/141388

PCT Pub. Date: Dec. 13, 2007

(65) Prior Publication Data

US 2009/0242779 A1 Oct. 1, 2009

(30) Foreign Application Priority Data

Jun. 5, 2006 (FI) .................................. 20060547

(51) Int. Cl.
*G01T 1/24* (2006.01)

(52) U.S. Cl. ................................................ 250/370.09

(58) Field of Classification Search ............ 250/370.09, 250/370.11
See application file for complete search history.

(56) References Cited

U.S. PATENT DOCUMENTS 5,677,940 A 10/1997 Suzuki et al.
5,784,429 A 7/1998 Arai
5,848,123 A 12/1998 Strömmer
6,586,743 B1 * 7/2003 Overdick et al. ....... 250/370.11

(Continued)

FOREIGN PATENT DOCUMENTS

| FI | 97665 | 11/1995 |
|---|---|---|
| WO | WO 01/23909 A1 | 9/2000 |
| WO | WO 01/69284 A1 | 3/2001 |

OTHER PUBLICATIONS

International Search Report for PCT/FI2007/050327 dated Oct. 4, 2007.

*Primary Examiner*—David P Porta
*Assistant Examiner*—Marcus H Taningco
(74) *Attorney, Agent, or Firm*—Stites & Harbison, PLLC; Juan Carlos A. Marquez, Esq

(57) ABSTRACT

The invention concerns an x-ray imaging sensor and an x-ray imaging method in which, in a scintillator element (11, 21) or in an element having a corresponding functionality, x-ray quanta are converted into photons having a wavelength substantially greater than the wavelength range of the x-ray quanta. The information detected in the scintillator element (11, 12) is converted to pixel-specific electric signals in a semiconductor element (13, 23), which includes photodiodes (15, 25, 35) or corresponding means that are arranged to divide at least part of the area of the sensor to pixels (14, 24, 34). Arranged in functional connection with the pixel-specific photodiodes (25, 35) or corresponding means, there has been arranged means comprising an I/F (current to frequency) converter (26, 36) or a corresponding component for quantizing the electric signals by converting them to pixel-specific frequencies, i.e. pulse trains.

29 Claims, 2 Drawing Sheets

Figure 1:
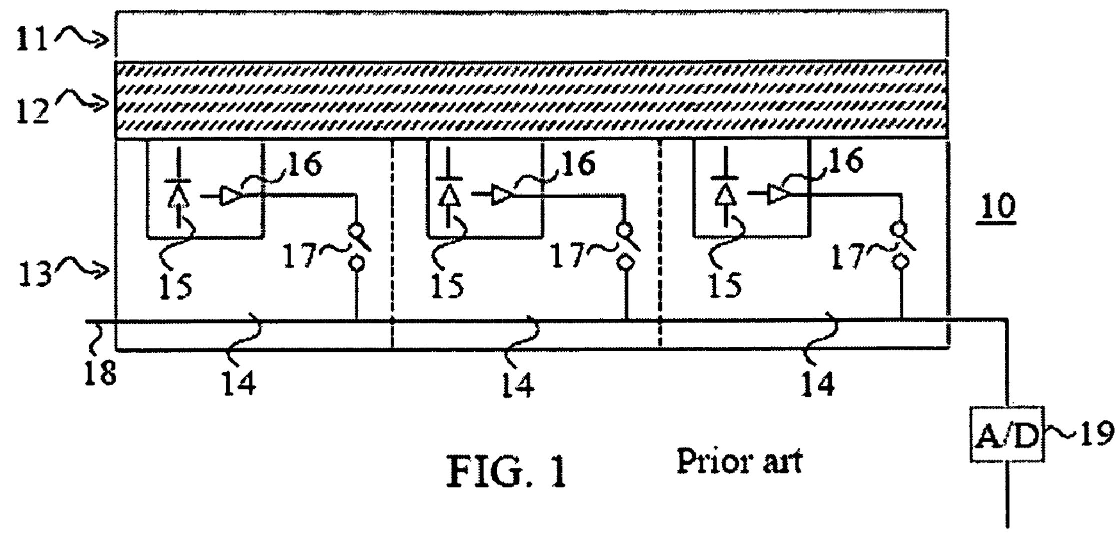

21
22
25
I/F
26
C
20
23
29
27
28
24
211

U.S. PATENT DOCUMENTS

| | | | |
|---|---|---|---|
| 6,906,749 | B1 | 6/2005 | Fox |
| 7,023,369 | B2 | 4/2006 | Bocko et al. |
| 2002/0141530 | A1 | 10/2002 | Vrettos et al. |
| 2005/0121617 | A1 | 6/2005 | Heismann et al. |

* cited by examiner

X-RAY IMAGING SENSOR AND X-RAY IMAGING METHOD

The present invention relates to an X-ray imaging sensor according to the preamble of claim 1 and to an X-ray imaging method according to the preamble of claim 14.

Electric imaging is increasingly replacing the traditional film-based X-ray imaging. In electric X-ray imaging, it is a long-standing practice to use a technology wherein X-ray quanta having penetrated the object being imaged are absorbed into a so-called scintillator, which in turn emits light photons, i.e. in a way converts the energy level of the X-ray quanta to a wavelength of light. The photons are transferred either directly or via a fiber-optic medium to a silicon substrate and, on being absorbed into the substrate, they form electron-hole pairs, i.e. charges detectable by electric means. Such a sensor can be divided into image elements, i.e. pixels, by various techniques. The pixel-specific signals are read and transferred into a memory and/or to a display via an A/D converter, which nowadays is typically placed in the sensor itself.

Imaging sensors are generally implemented using CCD and CMOS sensor technologies, which have their advantages and disadvantages. For example, CMOS technology is in many respects a better alternative than CCD because, among other things, it makes it possible to achieve a greater degree of integration of functions, a lower energy consumption and, thus, a construction that is smaller and can be implemented at a lower cost. However, the use of CMOS technology e.g. in so-called TDI (Time Delay Integration) imaging has so far been impossible in practice because in CMOS sensors it has been possible to read the information of each pixel from the sensor as independent pixel-specific signals only, and thus it has not been possible to track the scanning movement of a beam in the object by transferring information from one pixel to another, as the TDI mode of operation requires.

It is known that TDI imaging can also be implemented at least in principle by using other than CCD technology. For example, in connection with sensors based on direct X-ray detection, in which the signal produced by X-ray quanta absorbed into a suitable medium such as CdTe is read directly as pulses detectable by pixel-specific counters, it is possible to arrange for counters to be loaded from other counters, and thus the scanning movement of the ray beam in the object used in TDI imaging can be tracked by a proper transferring of the contents of the counters from each other. This technology is described e.g. in WO specification 01/69284. However, the development of this sensor technology, based on so-called direct detection, has at least so far not reached quite the level of practical implementation, due among other things to the high price of the X-ray quanta absorbing materials used in this technology. Furthermore, the so-called bump-bonding technology used in the manufacture of these devices is technically difficult to implement and therefore expensive as well.

Some sensor solutions based on CMOS technology are described in US patent specifications U.S. Pat. Nos. 6,906,749 and 7,023,369. Of these, the former deals with a complicated electronics arrangement which is described as allowing TDI imaging to be performed even by using a CMOS sensor but which requires, among other things, twice as large a surface area than a corresponding CCD sensor. Pixel signals are processed in analog form which, as compared to digital technology, involves losses and disturbances, additional noise and distortion of signals. The specification does not deal with X-ray imaging sensors, nor does the above-mentioned specification U.S. Pat. No. 7,023,369, which is concerned with digitalization of a pixel signal by sigma-delta conversion. U.S. Pat. No. 7,023,369 does not teach a sensor applicable for TDI imaging.

The object of the present invention is to create a new type of X-ray imaging sensor in which it is possible to use the existing and in many ways advantageous CMOS technology while still, among other things, utilizing many advantages of digital technology. The invention aims at achieving an X-ray imaging sensor and an X-ray imaging method that will reduce problems encountered in many prior-art solutions, regarding processing of information present in a charge-form, but in such a way, however, that enables use of components according to the more traditional technology of a relatively simple construction and thus ending up with an arrangement that can be implemented relatively economically. In particular, the invention provides a new type of possibility to implement TDI imaging even in imaging based on CMOS technology.

The essential features of the invention are presented in the attached independent claims, and some of its preferred embodiments are presented in the attached dependent claims. Thus, the invention is based on a solution where pixel-specific information is quantized on the pixel level and transferred into pixel-specific counters or corresponding chargeable components in a construction where the sensor is still implemented in a considerably simpler and cheaper way as compared to the so-called direct-detection technology. As the pixel-specific information is quantized already at the pixel level, preferably expressly in an I/F (current to frequency) converter, the traditional separate A/D converter (or a number of them) is not needed at all in the solution of the invention.

Figure 2:
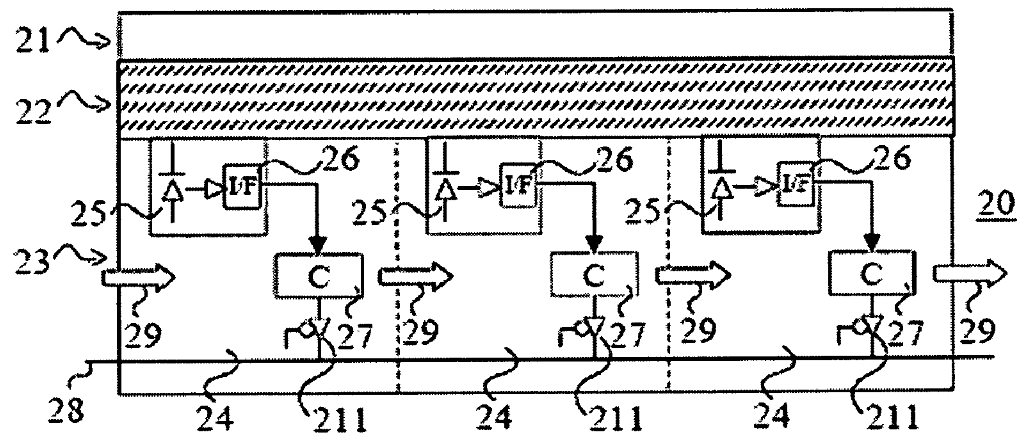
Figure 3:
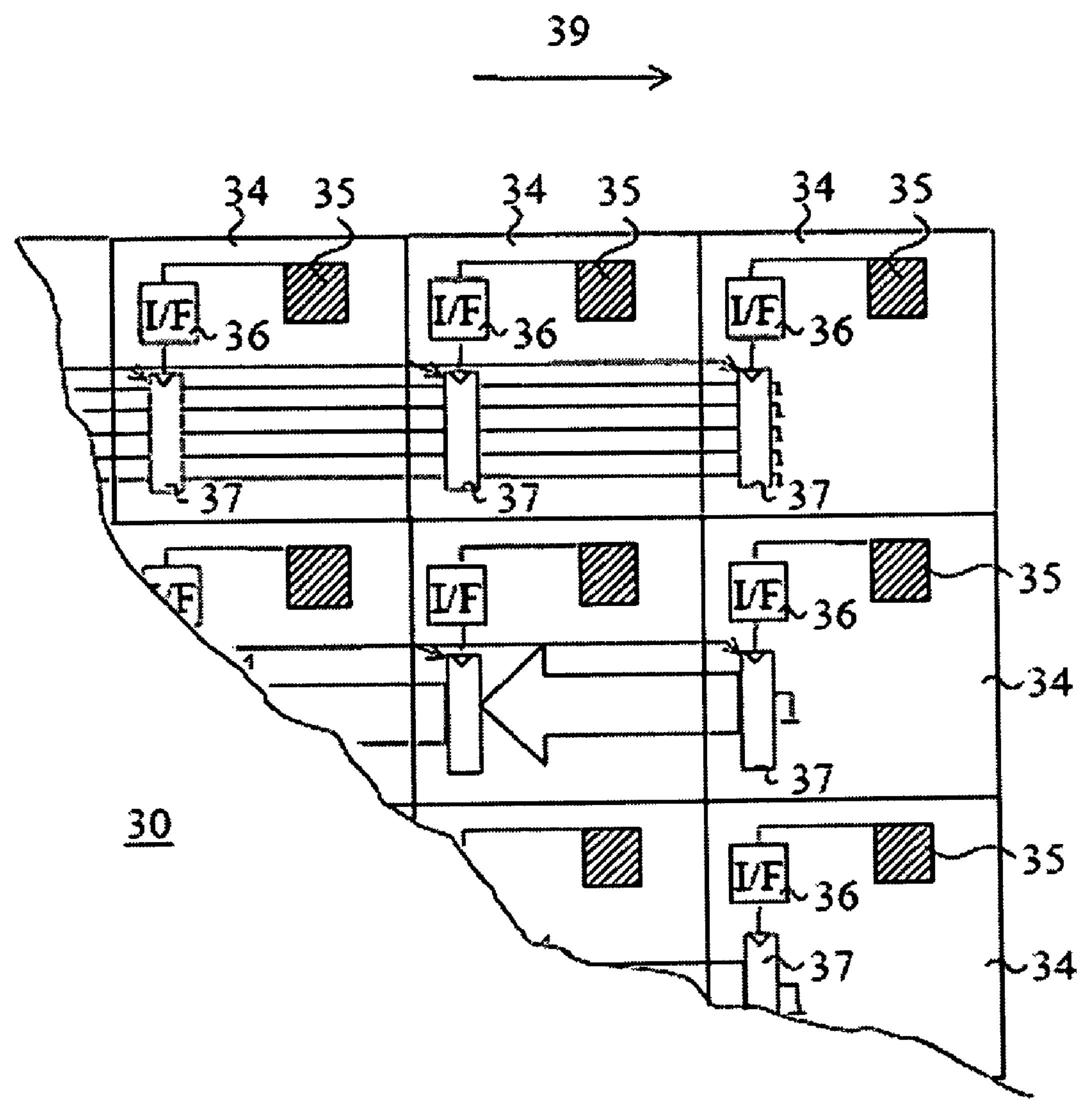

In the following, the invention and some of its preferred embodiments will be described by also referring to the attached FIGURES, of which FIG. 1 represents a conventional CMOS-type sensor in side view, illustrating the principle of its construction, FIG. 2 represents a principled side view of one preferred embodiment of the sensor of the invention, and FIG. 3 illustrates a pixel arrangement in one sensor according to the invention that enables TDI imaging.

FIG. 1 presents a cross-sectional side view of a typical sensor 10 based on conventional CMOS technology, used in X-ray imaging. Such a sensor typically comprises a scintillator layer 11, which receives X-radiation and converts X-ray quanta into photons in the visible light wavelength range, and a fiber-optic plate 12 positioned over a semiconductor element 13 comprising the CMOS circuit itself. The pixels 14 provided in the semiconductor element 13 comprise a photodiode 15 and an analog CMOS circuit connectable via a switch 17 to an analog electronic reading circuit 18 common to all the pixels 14. The pixel-specific electronic circuit may be implemented in various ways; in the solution according to FIG. 1, it comprises a buffer transistor 16. The signal obtained from the electronic reading circuit 18 is transferred out of the sensor via an A/D converter 19.

In the sensor according to FIG. 1, the pixel signals are read out one at a time by connecting the pixels 14 via the pixel-specific switches 17 one after the other to the reading circuit 18. The reading of the pixel-specific information is a destructive action and further, in a sensor of this type it is not possible to transfer or add the pixel signal, which is in a charge-form, to another pixel.

FIG. 2 represents one preferred embodiment of the present invention, wherein the sensor 20 also comprises a scintillator layer 21 or an element having a corresponding functionality, which converts X-ray quanta into photons having a wavelength substantially greater than the wavelength range of the X-ray quanta, and a fiber-optic plate 22 comprising a CMOS circuit, positioned over a semiconductor element 23. Instead of an analog electronic circuit connected to photodiodes 25 or corresponding means, the pixels 24 comprise means comprising an I/F converter (current-to frequency converter) 26 or a corresponding component for converting the pixel-specific electric signal into a pixel-specific frequency, i.e. pulse train, and a counter 27 connected to the I/F converter and arranged to integrate this pulse train. According to the invention, the sensor 20 is arranged to comprise at least one pixel column; FIG. 2 represents one pixel row in an embodiment comprising several pixel columns.

In the solution according to FIG. 2, the counters 27 are arranged to be read via a common output bus 28, in which case the sensor is provided with pixel-specific selecting elements 211 (such as so-called three-state buffers) for reading one pixel signal at a time, but, in addition to or instead of this, each counter 27 can preferably be arranged to be loaded e.g. from the corresponding counter in the previous pixel row (arrows 29 in FIG. 2). Such an arrangement makes it possible to use the sensor of the present invention, based on CMOS technology, for TDI imaging as well, in which case the sensor signal can be read out e.g. via a shift register provided beside the outermost pixel column of the sensor or directly from the counters in the last column. Further, it is possible to use an arrangement where the counters 27, besides being loaded in one direction, can also be loaded in both directions, allowing the sensor to be used for TDI imaging in opposite directions. The information may be also arranged to be read out from the counters 27 in a given pixel column. In the CMOS sensor illustrated in FIG. 2, the information is thus already converted into pulse form in the pixels 24. Consequently, the pixel signals can be processed as digital signals and the sensor signal can be read out directly in digital form without a separate, such as external A/D conversion.

The counters 27 may be frequency or pulse counters, preferably multi-bit counters. They can also be arranged to be physically disposed elsewhere on the sensor than directly in the active region of the sensor, in other words, they can be placed in a region other than the area where the pixels 24, and therefore the pixel-specific photodiodes 25 or components having a corresponding functionality, are located.

The counters 27 can be provided with a circuit that prevents counting when the counter has reached its maximum numeric value, whereupon overexposure will not produce in the image any other error except that the measured pixel signal is at its maximum value. On the other hand, the counters can be implemented as a version having a sufficient number of bits, and/or the sensitivity of the I/F converter can be arranged to be adjustable so that in practice, overexposure can not occur at all.

In the construction according to the invention, it is possible to use either a linear or a non-linear, such as logarithmic I/F converter. In view of the preferred embodiment of the invention, the utilization of the invention to permit TDI imaging even in a sensor based on CMOS technology, the converter is implemented as a linear I/F converter.

In this connection, the term I/F converter refers in its widest sense to any functional component or arrangement that is capable of quantizing the electric signal obtained from a photodiode or equivalent into a frequency, i.e. into a pulse train. The dark frequency resulting from the dark current of I/F converters which typically are applicable for use in the invention, is a few hundred Hz or lower, because higher frequencies already begin to affect the dynamic range available. On the other hand, when it is expedient to reach dynamics of at least 3 decades, such as 4 decades in practice in view of certain conceivable dental embodiments of the invention, the frequency range of the I/F converter used in the solution of the invention is preferably e.g. 10 Hz-100.000 Hz or 100 Hz-1.000.000 Hz.

Concerning applying the invention to TDI imaging, the frequency range of the I/F converters is preferably adapted taking into account the stepping frequency used in TDI imaging and the pixel-specific counters used in the sensor. Then, it is preferable to arrange the frequency corresponding to the dark current of the I/F converter to be substantially of such an order that, during one TDI cycle, at least a few pulses can be stored in the pixel-specific counters even at low signal levels, because if the frequency range of the I/F converter is too low in this respect, then quantizing noise will be produced when the signal at low signal levels becomes too "grainy" in proportion.

It is thus possible to provide the sensor of the invention with means for controlling the operation of the I/F converters. The control can be arranged to be effected on the basis of control signals applied to the sensor from outside or e.g. automatically on the basis of a signal generated from the radiation detected by the sensor. For example, if the sensor signal is found to be increasing beyond the optimal level during imaging, then the sensor dynamics can be optimized by reducing the sensitivity of the I/F converter, e.g. by adjusting the conversion gain, such as the reference voltage of the converter. Correspondingly, the sensitivity can naturally also be increased if necessary. In view of image formation, for the implementation of such autonomic control, it is naturally also necessary to provide the sensor assembly with means for delivering information regarding these adjustments carried out so that the changes in parameter values can be correctly taken into account by software in image formation.

A sensor according to the invention can be arranged to comprise at least two pixel columns and the counters (27, 37) be arranged to be read each independently and/or so that the counters (27, 37) for the pixels (24, 34) on the same rows are each arranged to be loadable from the respective counter (27, 37) in the previous column on the corresponding row. At least a part of the counters (27, 37) can be arranged to be controllable so that they start integration either from zero or from a value loaded into them from another counter. Value "zero" in this context may mean also some other constant preset value than specifically the integer zero. Further, at least some of the aforesaid counters (27, 37) can be arranged to start the integration each time from a value loaded into them from another counter (27, 37).

FIG. 3 represents one preferred embodiment of the invention. For each pixel 34 and associated photodiode 35, a separate I/F converter 36 is provided. The pixel-specific counters 37 are connected to each other in the direction 39 of the imaging scan so that, to allow easier reading out of the result of the counters 37 and, on the other hand, also to enable TDI imaging, the counter 37 of each pixel 34 is loadable in parallel from the counter 37 of the pixel 34 in the previous pixel column on the same row. The counters 37 in the first column, for example, can be arranged to be loaded to zero. This allows the sensor signal to be easily reset. In connection with TDI imaging, the solution of the invention thus comprises means for controlling the sensor in such a way that the counters 37, controlled by control signals, periodically integrate, on the one hand, and transfer/receive signals from the other counters 37, on the other hand. As noted, the arrangement can also be implemented in such a manner that the reading direction of the signal (or of the TDI) can be electrically reversed, which allows imaging in TDI mode in either direction.

The sensor electronics can be implemented in a way that allows the results of the outermost counters to be loaded in parallel into a shift register provided beside the outermost pixel column—in view of TDI imaging, into a shift register disposed expressly on the trailing edge side of the sensor—the shift register being further arranged to shift out the bits of one row serially in sequence. Such a sensor can be used for both full-field imaging and TDI imaging in which case, at its minimum, for the output of all the image data produced by the sensor only one output signal is needed. Shift registers can also be provided on both edges of the sensor.

The first end of the shift register can be arranged to load in serial data e.g. from another identical module comprised in the same sensor arrangement. Thus, the image information detected by a sensor consisting of a plurality of separate modules can be arranged to be read out via only one signal line.

If a sufficiently small physical pixel size has been chosen for the sensor, then the pixel signals read out can be combined to form larger entities e.g. in a computer reserved for image processing. The image signal can also be processed to increase resolution in the direction of movement in TDI imaging, and so the dose of radiation resolution required by each object to be imaged can be optimized to a desired value, as described e.g. in FI patent 97665.

It is also possible to connect to the end of each pixel row an adder circuit that sums up a desired number of numeric pixel values before they are loaded into the shift register. When a similar adder circuit is attached to the output end of the shift register to add up a desired number of numeric pixel values that may be shifted out, the sensor circuit will be able to directly accomplish pixel binning in X and Y directions, i.e. combining pixels to form larger pixels. As the signal can be read out directly from the sensor of the invention, e.g. from the outermost pixel column, i.e. without providing it with a separate shift register, such an adder circuit can naturally also be provided in connection with any such pixel column intended for reading out the signal.

Especially when the technology of the invention is to be used in connection with dental scanning imaging, a preferred embodiment of the invention comprises a sensor whose dimensions as a whole are of the order of 10 mm×150 mm but which, instead of being implemented as a monolithic device, consists of several modules comprising a CMOS circuit. The electronics of such modules are preferably so arranged that when the modules are of rectangular shape and have dimensions of the order of e.g. 10×20 mm the “dead” area of them, as far as detection of image information is concerned, is arranged to be as small as possible, expressly at the short edges of the modules. Such a configuration allows the modules to be more easily arranged one after the other with as small gaps between them as possible. For optimal combination of signal-to-noise ratio, resolution, sensitivity, number of components and other properties, the pixel size used in the modules in the aforesaid direction of the short side, i.e. in practice in the scanning direction of the sensor, is preferably of the order of 30-50 μm, in the vertical direction substantially the same or up to the order of 100 μm. The pixel-specific counters used in the sensor are preferably multi-bit counters consisting of at least 6 bits, such as 18-bits and, according to this preferred embodiment of the invention, the maximum frequency of the I/F converter is e.g. of the order of 400 kHz. Thus, during imaging, there is no great risk of counter overflow, i.e. of the counter reaching full cycle, even in the case of the longest integration times typically used. The stepping speed in TDI imaging, in other words the pixel-to-pixel transfer or TDI frequency, may be arranged to be of the order of 300-800 Hz.

A counter can certainly also be provided with a mechanism for preventing overflow, but then again, the number of bits in the counters may also be easily increased with the same complexity, as each addition of bits doubles the dynamics of a counter. Besides, it is also possible to arrange in connection with the counter a mechanism for warning about a possible imminent overflow and means for adjusting the functions of the sensor on the basis of this.

In another preferred dental embodiment of the invention, the pixel size of the sensor is arranged to be below 30 μm or less. The connection solutions for the sensor are preferably arranged to detect whether the highest bit of any counter integrating image information has changed to “one” to indicate that, in one of the pixels, over half of the maximum dynamic range has been used up. In this way, based on such a signal received from a sensor especially applicable for intra-oral X-ray imaging, irradiation can be terminated and over-exposure effectively prevented, even if the irradiation would not be quite immediately stopped on the basis of the control signal given.

One of the advantages provided by the invention, especially in connection with intra-oral imaging, is that it allows the image information to be read out from the sensor without any special haste, because the entire image is stored in digital form such that it will not be degraded as a function of time e.g. due to dark currents or noise, even if the information is read out slowly. The information may also arranged to be readable out again and again.

Further, the counters can be arranged to include either binary, grey code or pseudorandom number generators. The counter type can be adapted according to the implementation, such as a pseudorandom sequence counter for small area sensors, or a straight binary counter in case adding or binning pixels.

In the above, the invention has been described by way of example by referring to its certain preferred embodiments. However, it is obvious to a person skilled in the art that, especially with the development of technology, the fundamental concept of the invention can be implemented in many different ways and that its different embodiments are not limited to the examples described above but can be varied within the scope of protection defined in the attached claims.

The invention claimed is:

1. X-ray imaging sensor, comprising a scintillator element converting X-ray quanta into photons having a wavelength substantially greater than the wavelength range of the X-ray quanta, or an element having a corresponding functionality, and a semiconductor element, which comprises a CMOS circuit, and photodiodes or corresponding means arranged to divide at least part of the surface area of the sensor into pixels to form at least one column, and to convert information detected in the aforesaid scintillator element into pixel-specific electric signals, wherein, arranged in functional connection with the aforesaid pixel-specific photodiodes or corresponding means, there is means comprising an I/F (current to frequency) converter, or a corresponding component for quantizing the aforesaid electric signals by converting them into pulse trains, and wherein the sensitivity of the aforesaid I/F converters is arranged to be adjustable on the basis of a signal applied from outside of the sensor or on the basis of a signal generated from the radiation detected by the sensor.

2. X-ray imaging sensor according to claim 1, wherein, arranged in functional connection with the aforesaid pixel-specific means comprising an I/F converter or a corresponding component, there is means for counting said pulse trains.

3. X-ray imaging sensor according to claim 2, wherein said pixel-specific counters are arranged to be physically disposed in a different area on the sensor than the pixel-specific photodiodes or equivalent.

4. X-ray imaging sensor according to claim 2, wherein the sensor is arranged to comprise at least two aforesaid pixel columns and the aforesaid counters are arranged to be read each independently and/or so that the counters for the pixels on the same rows are each arranged to be loadable from the respective counter in the previous column on the corresponding row, the information being arranged to be read out from the sensor either from the counters in a given pixel column, such as an outermost pixel column, or via a shift register provided.

5. X-ray imaging sensor according to claim 4, wherein loading of the counters as well as other sensor structures and components required at a given time are arranged to enable the sensor to be operated in opposite TDI imaging directions.

6. X-ray imaging sensor according to claim 4, wherein an adder circuit is provided between each of the pixels of an outermost pixel column and a shift register, and/or at the output end of the aforesaid pixel column arranged to be used for reading out the signal.

7. X-ray imaging sensor according to claim 4, wherein at least a part of the aforesaid counters are arranged to be controllable so that they start integration either from zero or from a value loaded into them from another counter, and/or that at least some of the aforesaid counters are arranged to start the integration each time from a value loaded into them from another counter and/or the counters are arranged to be such that they will not continue counting after having reached their maximum numeric value.

8. X-ray imaging sensor according to claim 4, wherein the sensor is arranged to be used in TDI imaging and the minimum frequency of the I/F converter has been made proportional to the stepping frequency in TDI imaging so that even a low pixel signal level will produce a few pulses at least.

9. An X-ray imaging sensor according to claim 2, wherein said means for counting said pulse trains is a frequency counter.

10. An X-ray imaging sensor according to claim 2, wherein said means for counting said pulse trains is a pulse counter.

11. An X-ray imaging sensor according to claim 2, wherein said means for counting said pulse trains is a multi-bit counters.

12. X-ray imaging sensor according to any one of claim 1, wherein the I/F converter is linear or logarithmic.

13. X-ray imaging sensor according to claim 1, wherein the I/F converter is arranged to be followed by a multi-bit counter consisting of at least 6 bits, such as 18-bits and/or is arranged to have a dynamic range of at least 3 decades, such as 4 decades.

14. X-ray imaging sensor according to claim 1, wherein the sensitivity of the aforesaid I/F converters are adjustable on the basis of said signal by controlling the conversion gain.

15. X-ray imaging sensor according to claim 1, wherein the sensitivity of the aforesaid I/F converters is arranged to be adjustable by controlling the conversion gain of the I/F converter.

16. X-ray imaging sensor according to claim 1, wherein the sensitivity of the aforesaid I/F converters is arranged to be adjustable by controlling the reference voltage of the I/F converter.

17. X-ray imaging method, wherein X-ray quanta are absorbed into a scintillator layer or an element having a corresponding functionality comprised in an imaging sensor, in which element they are converted into photons having a wavelength substantially greater than the wavelength range of the X-ray quanta, said photons being passed to a semiconductor element containing a CMOS circuit and comprising photodiodes or corresponding components which divide at least part of the surface area of the sensor into pixels to form at least one column, in which photodiodes pixel-specific information is converted into electric signals, wherein the aforesaid electric signals are quantized by an I/F (current to frequency) converter or by means comprising a corresponding component by converting them into pulse trains, and wherein the sensitivity of the aforesaid I/F converters is arranged to be adjustable on the basis of a signal applied from outside of the sensor or on the basis of a signal generated from the radiation detected by the sensor.

18. X-ray imaging method according to claim 17, wherein said pulse trains are integrated by means of.

19. X-ray imaging method according to claim 18, wherein the highest bits of at least some of the counters are monitored so as to obtain information as to whether an overflow of the counter is imminent.

20. X-ray imaging method according to claim 18, wherein the counters are loaded pixel row by pixel row optionally either in a first direction or in a second direction.

21. X-ray imaging method according to claim 18, wherein said pulse trains are integrated by means of a frequency counter.

22. X-ray imaging method according to claim 18, wherein said pulse trains are integrated by means of a pulse counter.

23. X-ray imaging method according to claim 18, wherein said pulse trains are integrated by means of a multi-bit counter.

24. X-ray imaging method according to any one of claim 17, wherein the imaging sensor used in the method is divided into pixels forming at least two columns and the sensor is used for TDI imaging by loading signals of counters during exposure into the counters of corresponding pixels in the next pixel column on the same row and by continuing integration from the value loaded into the counter from another counter.

25. X-ray imaging method according to claim 24, wherein, when the counters are being loaded, a zero value is loaded into the counters of the pixels in the first column.

26. X-ray imaging method according to claim 24, wherein signals integrated by the counters are added up in the direction of the pixel rows before the signal is transferred into the shift register and/or while the signal is being read out.

27. X-ray imaging method according to claim 14, wherein the counter signals are read out from the outermost pixel column or via a shift register provided beside it.

28. X-ray imaging sensor, comprising a scintillator element converting X-ray quanta into photons having a wavelength substantially greater than the wavelength range of the X-ray quanta, or an element having a corresponding functionality, and a semiconductor element, which comprises a CMOS circuit, and photodiodes or corresponding means, arranged to divide at least part of the surface area of the sensor into pixels to form at least one column, and to convert information detected in the aforesaid scintillator element into pixel-specific electric signals, wherein, arranged in functional connection with the aforesaid pixel-specific photodiodes or corresponding means, there is means comprising an I/F (current to frequency) converter or a corresponding component for quantizing the aforesaid electric signals by converting them into pulse rains, and wherein the sensor is arranged to be used in TDI imaging and the minimum frequency of the I/F converter is arranged proportional to the stepping frequency in TDI imaging so that even a low pixel signal level will produce a few pulses at least.

29. X-ray imaging method, wherein X-ray quanta are absorbed into a scintillator layer or an element having a corresponding functionality comprised in an imaging sensor, in which element they are converted into photons having a wavelength substantially greater than the wavelength range of the X-ray quanta, said photons being passed to a semiconductor element containing a CMOS circuit and comprising photodiodes or corresponding components which divide at least part of the surface area of the sensor into pixels to form at least one column, in which photodiodes pixel-specific information is converted into electric signals, wherein the aforesaid electric signals are quantized by an I/F (current to frequency) converter or by means comprising a corresponding component by converting them into pulse trains, wherein said pulse trains are integrated by means of frequency or pulse counters, and wherein the highest bits of at least some of the counters are monitored so as to obtain information as to whether an overflow of the counter is imminent.

* * * * *